United States Patent
Wolff et al.

(10) Patent No.: US 6,325,767 B1
(45) Date of Patent: Dec. 4, 2001

(54) STRENGTH MEASURING DEVICE FOR THE MEASUREMENT OF MUSCLE STRENGTH OF SINGULAR MUSCLE GROUPS OF AN INDIVIDUAL

(76) Inventors: Hartmut Wolff, Bachumer Weg 70, 59757 Arnsberg; Dieter Lagerstrøm, Triererstrasse 48, 50858 Köln; Erhard Peuker, Arns Weide 7, 59757 Arnsberg, all of (DE)

( * ) Notice: Subject to any disclaimer, the term of this patent is extended or adjusted under 35 U.S.C. 154(b) by 0 days.

(21) Appl. No.: 09/390,180

(22) Filed: Sep. 7, 1999

(30) Foreign Application Priority Data

Sep. 8, 1998 (DE) .............................................. 198 40 800

(51) Int. Cl.[7] .................................................. A61B 5/103
(52) U.S. Cl. ........................................ 600/587; 73/379.01
(58) Field of Search .................................... 600/587, 594, 600/595; 73/379.01, 379.03; 482/8, 9, 91, 92, 903

(56) References Cited

U.S. PATENT DOCUMENTS

| | | | | |
|---|---|---|---|---|
| D. 321,023 | * | 10/1991 | Schultz | D21/191 |
| 3,752,144 | * | 8/1973 | Weigle, Jr. | 128/2 S |
| 4,492,236 | * | 1/1985 | Pile | 600/587 |
| 4,702,108 | * | 10/1987 | Amundsen et al. | 73/379 |
| 4,742,832 | * | 5/1988 | Kauffmann et al. | 128/774 |
| 5,029,592 | * | 7/1991 | Schultz | 128/774 |
| 5,335,674 | * | 8/1994 | Siegler | 128/782 |
| 5,474,086 | * | 12/1995 | McCormick et al. | 128/782 |
| 5,662,591 | * | 9/1997 | Peindl et al. | 601/24 |
| 5,667,460 | * | 9/1997 | Smith | 482/8 |
| 5,997,440 | * | 12/1999 | Hanoun | 482/10 |
| 6,227,047 | * | 5/2001 | Livingston | 73/379.08 |

* cited by examiner

Primary Examiner—Eric F. Winakur
Assistant Examiner—Charles Marmor, II
(74) Attorney, Agent, or Firm—Sierra Patent Group Ltd

(57) ABSTRACT

A device for measuring the force-exerting ability of human muscle groups, comprising at least one pressing element which works together with a force-measuring unit which can measure the force exerted on at least one pressing element The pressing element, of which there is at least one in the force-measuring unit. being arranged so that its height can be adjusted and so that it can be fixed at a desired height. The force-measuring device having, in addition to the at least one pressing element working together with a force-measuring unit, at least one and preferably three additional pressing elements serving to hold certain parts of the test person's body in place, whose height can also be adjusted and which can be fixed at the desired height and are horizontally adjustable and can be fixed in the desired horizontal position.

25 Claims, 4 Drawing Sheets

STRENGTH MEASURING DEVICE FOR THE MEASUREMENT OF MUSCLE STRENGTH OF SINGULAR MUSCLE GROUPS OF AN INDIVIDUAL

BACKGROUND OF THE INVENTION

1. Field of the Invention

This invention concerns a force-measuring device, in particular a device for measuring the force-exerting ability of human muscle groups, comprising at least one pressing element which works together with a force-measuring unit which can measure the force exerted onto at least one pressing element, with this pressing element (of which there is at least one) in the force-measuring unit being arranged so that its height can be adjusted and so that it can be fixed at a desired height.

2. The Background Art

Force-measuring devices of the type described at the beginning are known from the state of the art as described in U.S. Pat. No. 4,742,832. For example, when measuring the force-exerting ability of the arm muscles, the subject is placed in sitting position in the force-measuring device. A load-producing cushion unit is located in front of the subject. When the subject presses his hand against the load-producing cushion unit, a motion is produced for measuring the force. The arrangement according to U.S. Pat. No. 4,742,832 simultaneously measures the force contributions of other muscle groups along with the force exerted by the muscle group which is to be measured. This falsifies the measurement.

In addition, there are force-measuring devices described in PCT/US 87/01247 and PCT/US 88/01354, which make it possible to measure various muscle groups. These systems have a complicated structure and are expensive. These systems also take up a lot of space. Moreover, even these force-measuring devices are unable to perform force measurements on individual muscle groups without simultaneously measuring the contributions of other muscle groups which are not supposed to be measured.

Measuring the force-exerting ability of various muscle groups is especially important for controlling the training of preventive medicine training programs. This concerns especially the trunk-stabilizing muscles, which have a special influence on the spinal column. Preventing back pain requires avoiding muscular imbalances. Sports medicine investigations have shown that weak trunk muscles favor the occurrence of back pain. Information about the ability force-exerting ability of the trunk muscles which determine performance is important for preventive medicine back training. Such information can help fitness centers, physical therapists, and other rehabilitation devices formulate individual training programs for customers or patients and target diagnosed muscular weaknesses. Such measurement procedures have seldom been used up to now for cost reasons, since creating the known measurement systems mentioned above was economically not very attractive.

SUMMARY OF THE INVENTION

The problem on which this invention is based is to create a measurement device of the type mentioned at the beginning which makes it possible to measure the force-exerting ability of individual muscle groups and is simultaneously simple to construct.

This is accomplished according to the invention by the fact that the force-measuring device has, in addition to the at least one pressing element working together with a force-measuring unit, at least one, preferably three pressing elements serving to hold certain parts of the test person's body in place, whose height can also be adjusted and which can be fixed at the desired height and are horizontally adjustable and can be fixed in the desired horizontal position. The individual muscle groups can be measured one after the other, with each of the pressing elements, of which there are at least one, being fixed at the height suitable for it.

It is also advantageous if at least one pressing element and/or the force-measuring device is arranged so that it can pivot upward and/or downward. This makes it possible, for example, to measure forces exerted onto the pressing element from above, so that the force-exerting ability of additional muscle groups can be determined.

It is preferable if the force-measuring device has two pressing elements, each working together with a force-measuring unit, with these two pressing elements being arranged so that they can be pushed horizontally, for example, against the breast and back of the subject at the same height. This makes it easy to measure the abdominal muscles and sacrospinal muscle one after the other, for example.

According to the invention, the force-measuring device can have, in addition to the at least one pressing element working together with a force-measuring unit, at least one, preferably three other pressing elements, which do not work together with a force-measuring unit and whose height can also be adjusted and which can be fixed at the desired height and preferably are also horizontally adjustable and which can be fixed in the desired position. These other pressing elements make it possible to hold the subject's body at certain places while other muscle groups are measured.

According to a preferred embodiment of this invention the force-measuring device comprises a frame with a top and two side frame pieces and a base plate from which the side frame pieces extend upward. Both sides of the side frame pieces which are turned toward one another can have a vertical adjustment strip arranged on them, on which vertical slides can move and be fixed, whose travel causes the height adjustment of the at least one pressing element. It is preferable if each of the vertical slides has a horizontal slide is fixed on it, in which a horizontal adjustment strip can move approximately in the direction toward the opposite vertical adjustment strip or away from it, with the movement of the horizontal adjustment strip causing the horizontal adjustment of the at least one pressing element. The frame construction with the horizontal and vertical adjustment strips and the vertical and horizontal slides assigned to them give the device a relatively uncomplicated structure, which nevertheless ensures that certain parts of the subject's body are fixed in an ideal manner for each muscle group and that the force is picked up in an ideal manner through the pressing elements.

The end of a horizontal adjustment strip turned toward the opposite vertical adjustment strip can have a force-measuring unit placed on it, on whose opposite end is placed the pressing element together with which it works. As an alternative to this, the end of a horizontal adjustment strip turned toward the opposite vertical adjustment strip can have a pressing element placed on it which does not work together with a force-measuring device. This makes it possible to move the pressing elements toward or away from the body of the subject by simply moving the horizontal adjustment strip horizontally.

According to a preferred embodiment of this invention, the force-measuring unit comprises a force transducer, which preferably has the shape of the letter "Z". The force transducer can measure the force exerted onto it, for example by means of a wire strain gauge. It is advantageous for the force transducer to work according to the principle of measuring shear force transverse to the longitudinal axis. Such a force transducer is very sensitive and can determine the force exerted on it over a great range of forces.

It is advantageous for the force-measuring unit to comprise a pivoting element which has a pressing element fastened to it by suitable means of attachment, with the pivoting element being arranged in the force-measuring unit in such a manner that exerting a force on the pressing element in the direction toward the force-measuring unit presses the pivoting element against the force transducer, and thus exerts a measurable force on it. The previously mentioned arrangement is constructed in a simple but effective manner since the force exerted on the pressing element is passed directly to the force transducer.

The horizontal and vertical slides can be placed on the horizontal and vertical adjustment strips in a continuously adjustable and fixable manner. As an alternative to this, equidistant holes can be made in the vertical and horizontal adjustment strips, which make it possible to fix the vertical or horizontal slides, in which case the vertical and horizontal adjustment can only be made in steps corresponding to the distances between the holes.

A force-measuring device according to the invention can also comprise horizontal and vertical stay bars. In particular, a horizontally oriented stay bar can be oriented perpendicular to the horizontal adjustment strips and can be gripped by the hands of the subject so that he can pull himself toward the bar or press himself away from it.

The following description of the figures also gives an overview of the muscle groups which can be measured, for example with the force-measuring device according to the invention. More advantages and features of this invention will be made clear by the following description of preferred embodiments, which makes reference to the attached figures. The figures are as follows:

DETAILED DESCRIPTION OF THE INVENTION

Figure 1:
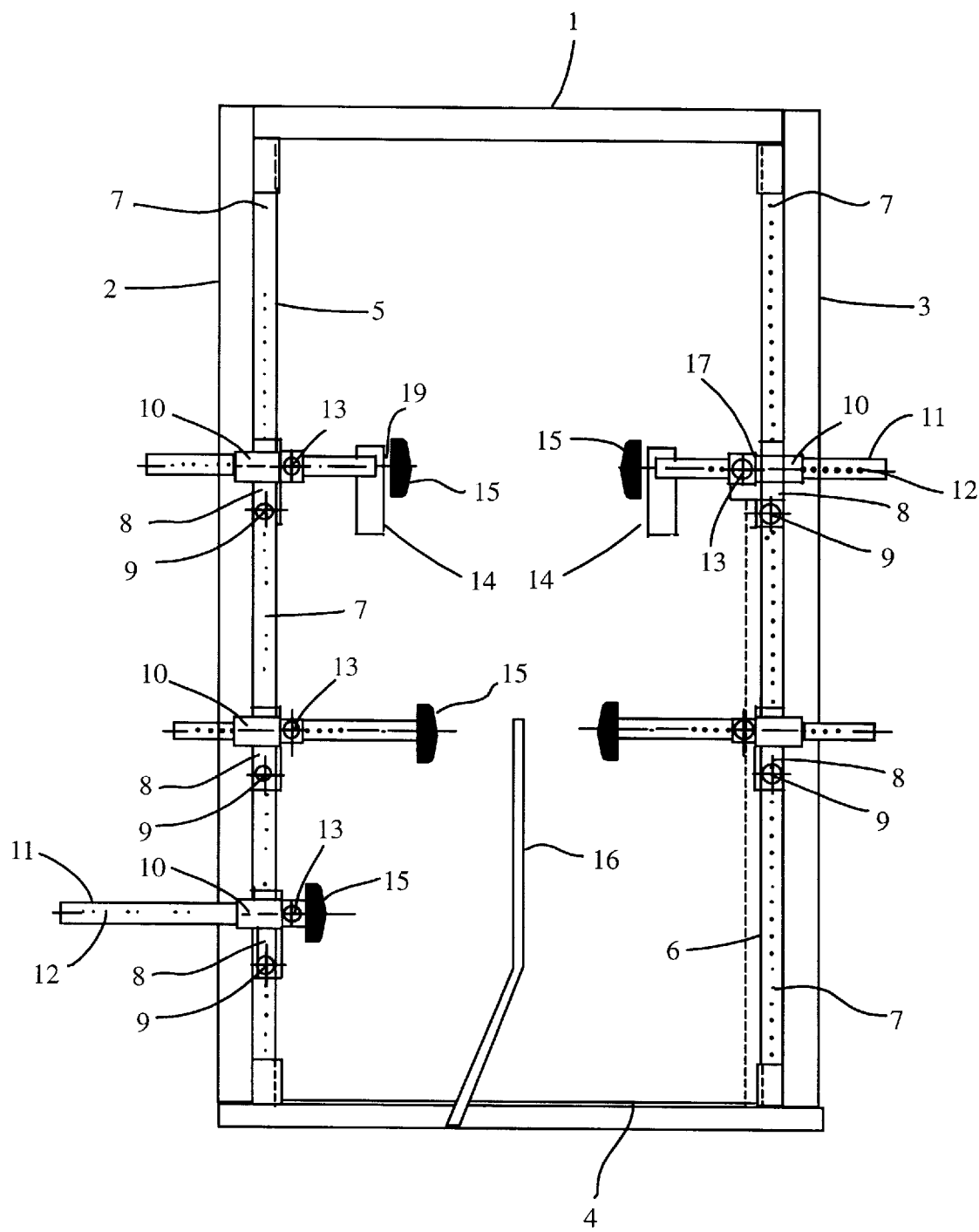
FIG. 1 is a front view of a force-measuring device according to the invention.

As can be seen in FIG. 1, a force-measuring device according to the invention comprises a frame made of a top frame piece 1 and side frame pieces 2, 3. The bottoms of the side frame pieces 2, 3 are connected with a base plate 4 which give a secure upright position to the force-measuring device according to the invention.

The internal sides of the side frame pieces 2, 3 turned toward one another have vertical adjustment strips 5, 6 placed on them which lie against them. The vertical adjustment strips 5, 6 can be designed as square metal struts, as are the frame pieces 1, 2, 3. In the sample embodiment shown, the vertical adjustment strips 5, 6 have equidistant holes 7 over their entire height, which, in the arrangement according to FIG. 1, pass through the adjustment strips 5, 6 from front to back and perpendicular to them. Each of the adjustment strips 5, 6 has several vertical slides 8 whose height can be adjusted, in particular which can slide up and down. The vertical slides 8 have a tightening knob 9 which makes it possible to fix the respective vertical slide 8 at the desired height as a function of the grid dimension of the holes 7 in adjustment strips 5, 6. Of course it is also possible according to the invention for the vertical slides 8 to be adjustable in a continuous manner, instead of stepwise, with the minimum step size being determined by the holes 7. In the sample embodiment shown, the left adjustment strip 5 has three vertical slides 8 arranged on it, while the right adjustment strip 6 only has two vertical slides 8.

Each of the vertical slides 8 has a horizontal slide 10 fastened on it which is oriented perpendicularly to it and through which a horizontal adjustment strip 11 can be moved approximately in the direction toward the middle of the force-measuring device and away from it, that is toward the left and right in FIG. 1. Each of the horizontal adjustment strips 11 has equidistant horizontal perpendicular holes 12 passing through the adjustment strip 11, so that the horizontal adjustment strip 11 can be stopped at a desired position by means of a tightening knob 13 arranged on the horizontal slide 10.

Each end of the two top horizontal adjustment strips 11 turned toward the middle of the force-measuring device has a force-measuring unit 14 according to the invention on it. This force-measuring unit 14 will be described in detail below. Each of the internal sides of the force-measuring device 14, which are turned approximately toward the middle of the force-measuring device, have pressing elements 15 made in the form of cushions placed on their upper third. Such pressing elements 15 made in the form of cushions are also located on the internal ends of the middle and lower horizontal adjustment strips 11 turned approximately toward the middle of the force-measuring device.

The force-measuring devices 14 and/or the pressing elements 15 can be arranged so that they can pivot, for example by up to 90°, about at least one point of articulation on the respective horizontal adjustment strip 11. This makes it possible to measure, for example, a force acting from above on the pressing element connected with a force-measuring device 14 after it is pivoted 90° counterclockwise.

FIG. 1 also shows another vertical stay bar 16 projecting upward from the base plate 4 and a horizontal stay bar 17 which is placed, in the sample embodiment shown, in the inside of the connection area of the top right vertical slide 8 with the associated horizontal slides 10. The function of the horizontal stay bar 17 is also described in detail below.

Figure 2:
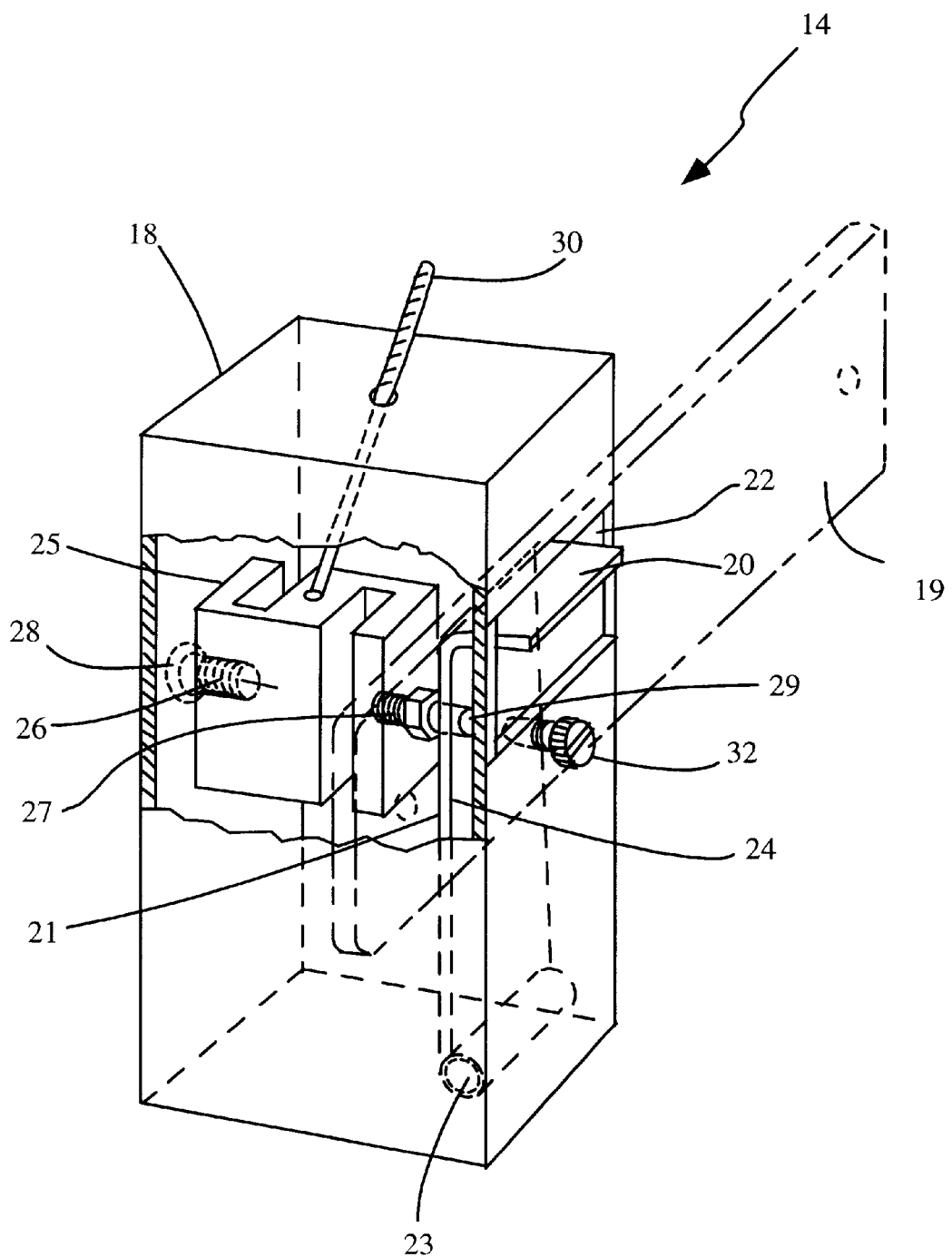
FIG. 2 is a perspective view of a force-measuring device according to the invention.

The force-measuring device 14 shown in detail in FIG. 2 comprises an essentially cuboid housing 18 whose side turned toward the inside or the middle of the force-measuring device has a cushion holder 19 placed on it. On the housing side, the cushion holder 19 is held approximately at its geometric center by an upper outward-turned leg 20 of a flat piece of steel 21 mounted in the housing so that it can pivot. The top L-leg 20 of the flat piece of steel 21 projects outward through a opening 22 in the inside of the housing 18, so that pressing on the pressing element 15 in the form of a cushion exerts a force through the cushion holder 19 onto the top L-leg 20 of the flat piece of steel 21. The lower part of the flat piece of steel 21 is mounted so that it can pivot about a pivoting axis 23. Starting from this pivoting axis 23, the flat piece of steel 21 comprises an essentially vertically oriented long leg 24 and the outward-oriented top L-leg 20 lying against it. Pressing on the pressing element 15 exerts an inward-directed force on the top L-leg 20, so that the essentially vertical leg 24 of the flat piece of steel 21 is also pressed inward.

The housing 18 also has a force transducer 25 placed in it, which is essentially Z-shaped. Each of the two outer right and left legs of the "Z" has a threaded hole 26, 27 in it. The threaded hole 26 makes it possible to fasten the force transducer 25 with a screw 28, for example, on the outside of the housing, approximately opposite the opening 22. In the sample embodiment shown in FIG. 2, the threaded hole 27 turned toward the inside holds an outward-facing screw 29 which runs to a point facing the vertical leg 24 of the flat piece of steel 21 and forming a pressure point for introducing force. An adjustment screw 32 makes it possible to adjust the distance between the vertical leg 24 of the flat piece of steel 21 and the pressure point of the screw 29 so as to minimize the play in the force-measuring unit 14.

The middle leg of the essentially Z-shaped force transducer 25 has a wire strain gauge placed in it, which makes possible sensitive measurement of the force exerted on the pressure point. The force transducer 25 works according to the principle of measuring shear force transverse to the longitudinal axis. The application space for the wire strain gauge can be filled with a highly elastic substance and thus be protected from mechanical and chemical damage. For example, on the top a measurement output 30 exits from the force transducer 25 and passes upward out of the housing 18 of the force-measuring unit 14, for example, as is shown in the sample embodiment. The measurement output 30 can be connected with a measurement device having an LCD display, for example. Such a measurement device can be powered by batteries or rechargeable batteries, for example, so that no external source of power is necessary. However, instead of being connected with a measurement device, the measurement output 30 can also be connected with a laptop computer, for example, or something like it, in order to store and further process the measurement data obtained.

Figure 3:
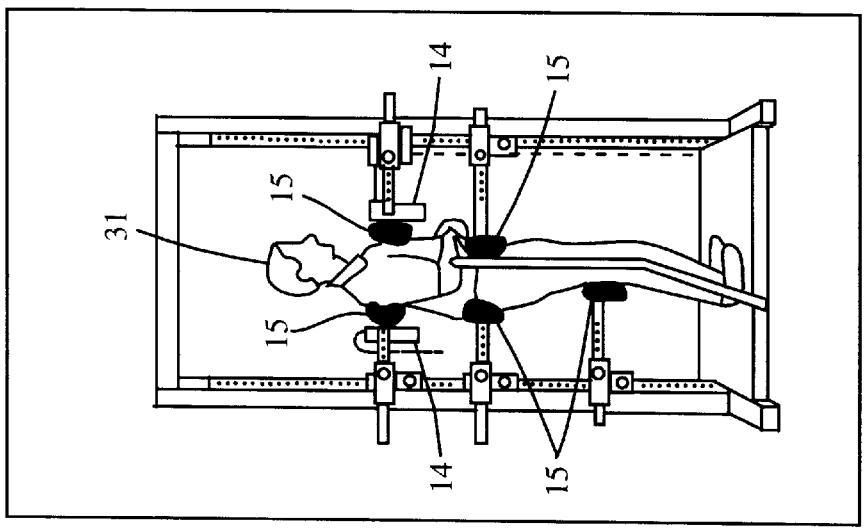
FIG. 3 is a perspective view of a force-measuring device according to the invention in an arrangement which is suitable for measuring the force-exerting ability of the abdominal muscles and the sacrospinal muscle.

FIG. 3 through FIG. 7 show sample applications of a force-measuring device according to the invention. The arrangement of the pressing elements 15 in the form of cushions shown in FIG. 3 is for measuring the force-exerting ability of the abdominal muscles and the sacrospinal muscle. In the sample embodiment shown the hip area of the subject 31 is fixed with the two middle pressing elements 15. The two left and right top pressing elements 15, each of which has a force-measuring unit 14, lie against the back and breast area of the subject 31. Pressing forward on the right force-measuring unit 14 measures the force-exerting ability of the abdominal muscles, while pressing backward on the left force-measuring unit 14 measures the force-exerting ability of the sacrospinal muscle.

Figure 4:
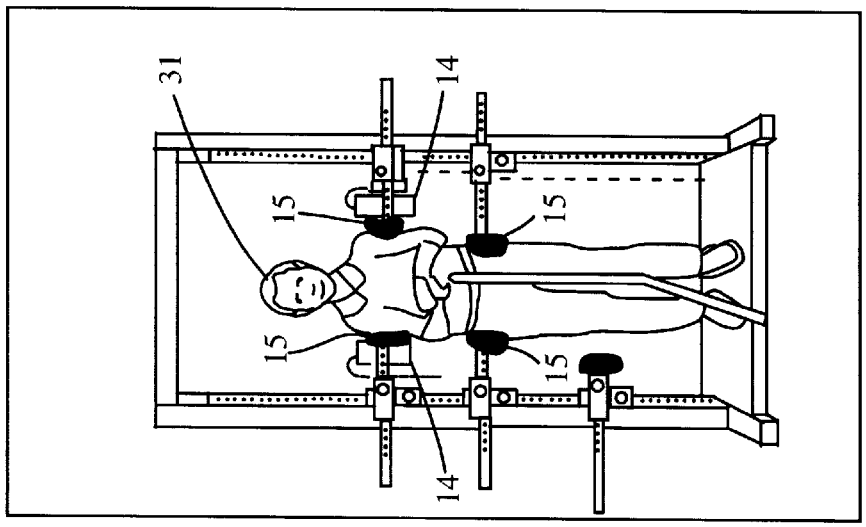
FIG. 4 is a perspective view of a force-measuring device according to the invention in an arrangement which is suitable for measuring the force-exerting ability of the side trunk muscles.

In the design shown in FIG. 4, the hips of the subject are again fixed by the middle pressing elements 15. The two top pressing elements 15, each connected with force-measuring units 14, lie against the top outside of the upper arms of the subject 31. Pressing to the left or right on the respective pressing elements 15 connected with force-measuring units 14 determines the force-exerting ability of the side trunk muscles (lateral flexion).

Figure 5:
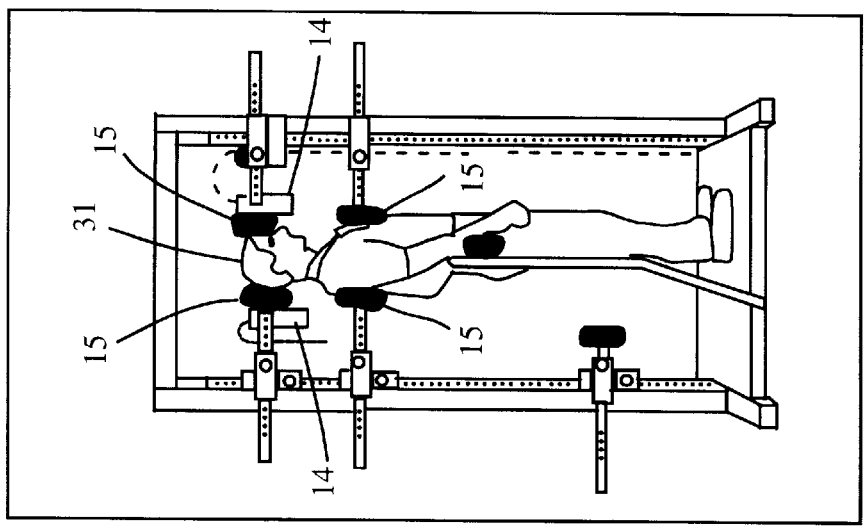
FIG. 5 is a perspective view of a force-measuring device according to the invention in an arrangement which is suitable for measuring the force-exerting ability of the flexors of the cervical spine and the cervical muscles.

In the arrangement shown in FIG. 5, the subject 31 is fixed approximately at breast height by the middle pressing elements 15. The pressing elements 15 connected with the force-measuring units 14 lie approximately in the area of the back of the head and the forehead. Pressing the forehead against the pressing element 15 in the form of a cushion on the right side of the force-measuring device according to the invention determines the force-exerting ability of the flexors of the cervical spine. Pressing the back of the head against the pressing element 15 in the form of a cushion on the left side of the force-measuring device according to the invention determines the force-exerting ability of the cervical muscles (extensors of the cervical spine).

Figure 6:
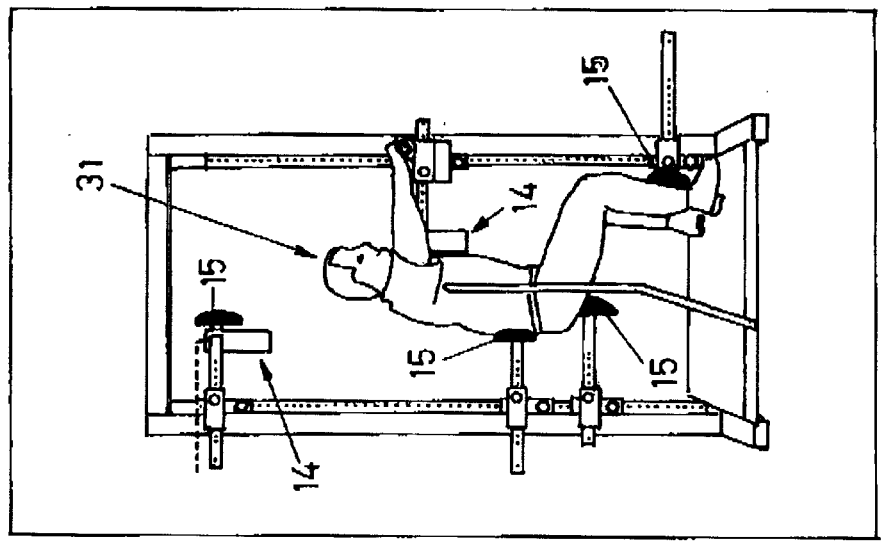
FIG. 6 is a perspective view of a force-measuring device according to the invention in an arrangement which is suitable for measuring the force-exerting ability of the upper back muscles and the triceps and pectoral muscles.

In the arrangement shown in FIG. 6, the lower left pressing element 15 made as a cushion serves as a sitting surface. The left pressing element 15 arranged above it stabilizes the lumbar spine of the subject 31, and the top right pressing element 15 connected with a force-measuring unit 14 lies against the breast area of the subject 31. The hands of the subject 31 grip the horizontal stay bar 17. Pulling the breast or the upper body against the pressing element 15 made in the form of a cushion in the right part of the force-measuring device determines the force-exerting ability of the upper back muscles. As an alternative to the arrangement shown in FIG. 6, the upper left pressing element 15 connected with a force-measuring unit 14 can be laid against the area of the shoulder blades of the subject 31. In such an arrangement if the arms are pressed forward against the stay bar 17, then pressing the back against the pressing element 15 made in the form of a cushion can determine the force-exerting ability of the triceps and pectoral muscles.

Figure 7:
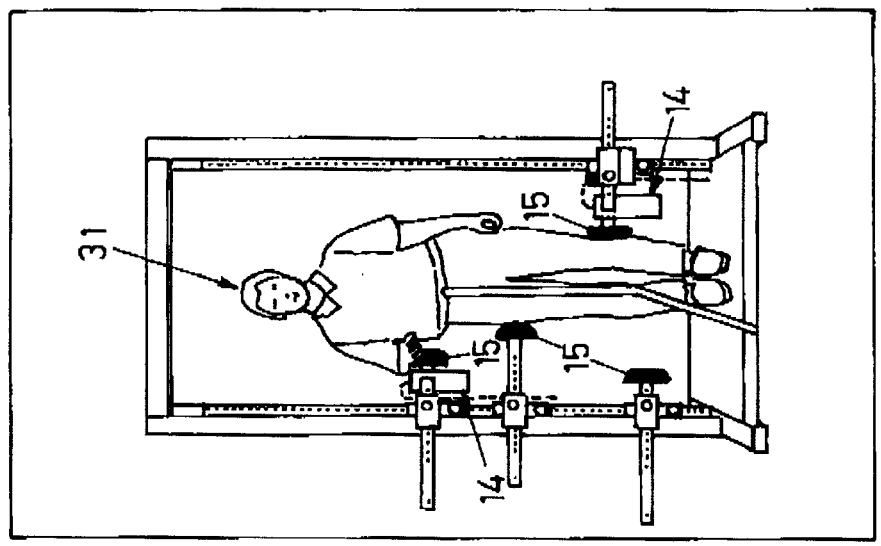
FIG. 7 is a perspective view of a force-measuring device according to the invention in an arrangement which is suitable for measuring the force-exerting ability of the abductor muscles.

In the arrangement shown in FIG. 7, the left middle pressing element 15 made in the form of a cushion lies in the outside area of the right thigh of the subject 31. Approximately in the area of the opposite knee the right pressing element 15 connected with a force-measuring unit 14 lies against it on the outside. Pressing the left leg against the cushion set at knee height makes it possible to determine the force-exerting ability of the abductors.

In addition to the muscle groups shown in FIG. 3 and FIG. 7, the force-measuring device according to the invention, with its great variability, can determine the force-exerting ability of other muscle groups

| List of Reference Numbers | |
|---|---|
| 1 | top frame piece |
| 2, 3 | side frame piece |
| 4 | base plate |
| 5, 6 | vertical adjustment strip |
| 7 | holes in 6 |
| 8 | vertical slide |
| 9 | tightening knob on 8 |

-continued

List of Reference Numbers

| | |
|---|---|
| 1 | horizontal slide |
| 11 | horizontal adjustment strip |
| 12 | holes in 11 |
| 13 | tightening knob on 10 |
| 14 | force-measuring unit |
| 15 | pressing element, cushion |
| 16 | vertical stay bar |
| 17 | horizontal stay bar |
| 18 | housing |
| 19 | cushion holder |
| 20 | top L frame piece |
| 21 | flat piece of steel |
| 22 | opening |
| 23 | pivoting axis |
| 24 | vertical frame piece |
| 25 | force transducer |
| 26, 27 | threaded hole |
| 28, 29 | screw |
| 30 | measurement output |
| 31 | subject |
| 32 | adjustment screw |

What is claimed is:

1. A device for measuring the force-exerting ability of human muscle groups, comprising:
    a plurality of pressing elements operatively coupled to respective force measuring units;
    said force measuring units configured to measure a force exerted substantially only on said pressing element that said force measuring units are coupled to;
    said force measuring units and said pressing elements being arranged on a frame so that their heights can be adjusted and fixed at a desired height; and
    at least one additional pressing element coupled to the frame, said additional pressing element having vertical and horizontal adjustability, said additional pressing element being configured to hold certain parts of the test person's body in place.

2. The force-measuring device according to claim 1, wherein at least one said pressing element is operatively coupled to a respective force measuring unit in said force-measuring device arranged so that said pressing element is horizontally adjustable and can be fixed in a desired horizontal position.

3. The force-measuring device according to claim 1, wherein at least one said pressing element is operatively coupled to a respective force measuring unit and can be rotated between 0 and 180 degrees.

4. The force-measuring device according to claim 1, wherein the force-measuring device comprises two pressing elements operatively coupled to respective force measuring units.

5. The force-measuring device according to claim 1, wherein said pressing elements are made in the form of cushions.

6. The force-measuring device according to claim 1, wherein the frame comprises a top and two side frame pieces and a base plate from which the side pieces extend upward.

7. The force-measuring device according to claim 6, wherein said two side frame pieces further include vertical adjustment strips on which a vertical sliding member is disposed, said vertical sliding member can be moved and fixed to said vertical adjustment strips, said movement makes adjusting the height of at least one pressing element possible.

8. The force-measuring device according to claim 7, wherein each of said vertical sliding members further includes a horizontal sliding member in which a horizontal adjustment strip having first and second ends can be moved relative to the opposite said vertical adjustment strip with the movement of the horizontal adjustment strip causing the horizontal adjustment of at least one pressing element.

9. The force-measuring according to claim 8, wherein said first end of said horizontal adjustment strip has a force-measuring unit and pressing element disposed thereabout, said force-measuring unit and said pressing element being rotatably affixed to said horizontal adjustment strip.

10. The force-measuring according to claim 9, wherein said first end of said horizontal adjustment strip further includes a pressing element, said pressing element being rotatably attached to said horizontal adjustment strip.

11. The force-measuring device according to claim 8, wherein said vertical and horizontal adjustment strips have equidistant apertures disposed therethrough, said apertures make affixing said vertical and horizontal slides to said vertical sliding members possible.

12. The force-measuring device according to claim 8, further including a stay bar whose height can be adjusted and which is oriented so that the stay bar is horizontal and perpendicular to the horizontal adjustment strips.

13. The force-measuring device according to claim 6, further including an essentially vertically oriented stay bar extending upward from said base plate.

14. The force-measuring device according to claim 1, wherein said force-measuring unit comprises a force transducer formed in the shape of the letter "Z".

15. The force-measuring device according to claim 14, wherein said force transducer measures the force exerted by means of a wire strain gauge.

16. The force-measuring device according to claim 14, wherein a magnitude of the force measured in the force transducer can be read through a measurement output.

17. The force-measuring device according to claim 14, wherein said force transducer works according to the principle of measuring shear force transverse to the longitudinal axis.

18. The force-measuring device according to claim 14, said force-measuring unit further comprises
    a pivoting element having a pressing element fastened to said pivoting element by suitable means of attachment, said pivoting element being arranged so that said pivoting element can pivot in a force-measuring unit in such a way that exerting a force on said pressing element in a direction toward the force-measuring unit presses said pivoting element against said force transducer thereby exerting a measurable force on said force transducer.

19. The force-measuring device according to claim 1, wherein said pressing elements coupled to said respective force measuring units are arranged above said additional pressing elements.

20. A device for measuring the force-exerting ability of human muscle groups, comprising:
    a first pressing element operatively coupled with a first force measuring unit configured to measure a force exerted only on said pressing element;
    a second pressing element opposing said first pressing element and operatively coupled with a second force measuring unit; and
    a frame for affixing said first and second pressing elements thereto,
    wherein each of said first and second pressing elements is horizontally and vertically adjustable relative to the frame for matching a bodily dimension of a test person, and wherein forces applied alternatively to each of said first and second pressing elements are measured by said first and second force measuring elements corresponding to muscular strengths of complementary muscle groups of said test person.

21. The device of claim 20, further comprising a third pressing element configured to contact the test person at a first contact position displaced along the length of the test person from a second contact position where said first and second pressing elements are configured to contact said test person for stabilizing said test person at said first contact position while said test person exerts a force at one of said first and second pressing elements.

22. The device of claim 21, further comprising a fourth pressing element opposing said third pressing element.

23. The device of claim 22, further comprising a fifth pressing element configured to contact the test person at a third contact position displaced along the length of the test person from each of said first and second contact positions for stabilizing said test person at said third contact position while said test person exerts a force at one of said first and second pressing elements.

24. A device for measuring the force-exerting ability of human muscle groups, comprising:
    a first pressing element operatively coupled with a first force measuring unit configured to contact a body of a test person at a first position;
    a second pressing element configured to contact said body of said test person at a second position;
    a third pressing element opposing said second pressing element and configured to contact said body of said test person at a third position opposite said second position; and
    a frame for affixing said first, second and third pressing elements thereto, and
    wherein at said first pressing element is vertically adjustable and said second and third pressing elements are horizontally adjustable to match a dimension of said body of said test person, and
    wherein said body of said test person is stabilized at said second and third positions when a force is exerted at said first pressing element.

25. A device for measuring the force-exerting ability of human muscle groups, comprising:
    at least three pressing elements configured to contact a body of a test person at a plurality of respective locations;
    a force measuring device coupled with a first of said pressing elements for measuring a force exerted in a first direction on said first pressing element by said body of said test person; and
    a frame for affixing each of said pressing elements thereto,
    wherein each of said pressing elements is adjustable along a line substantially parallel to said first direction to match a dimension of said body of said test person, and
    wherein each of said at least three pressing elements exerts a force in a direction along a line substantially parallel to said first direction, such that said body of said test person remains in place while said force is exerted on said first pressing element.

* * * * *